US009642356B2

(12) United States Patent
Wood et al.

(10) Patent No.: US 9,642,356 B2
(45) Date of Patent: May 9, 2017

(54) MATURATION OR RIPENING INHIBITOR RELEASE FROM POLYMER, FIBER, FILM, SHEET OR PACKAGING

(75) Inventors: Willard E. Wood, Arden Hills, MN (US); Neil J. Beaverson, Vadnais Heights, MN (US); William J. Kuduk, Minneapolis, MN (US)

(73) Assignee: Cellresin Technologies, LLC, Bloomington, MN (US)

( * ) Notice: Subject to any disclaimer, the term of this patent is extended or adjusted under 35 U.S.C. 154(b) by 0 days.

(21) Appl. No.: 12/967,226

(22) Filed: Dec. 14, 2010

(65) Prior Publication Data

US 2011/0143004 A1    Jun. 16, 2011

Related U.S. Application Data

(60) Provisional application No. 61/286,177, filed on Dec. 14, 2009.

(51) Int. Cl.
| | | |
|---|---|---|
| A23B 7/00 | (2006.01) |
| B65D 90/00 | (2006.01) |
| C09K 15/06 | (2006.01) |
| A01N 3/00 | (2006.01) |
| A01N 3/02 | (2006.01) |
| A23B 7/154 | (2006.01) |
| B65D 81/24 | (2006.01) |

(52) U.S. Cl.
CPC .............. A01N 3/00 (2013.01); A01N 3/02 (2013.01); A23B 7/154 (2013.01); B65D 81/24 (2013.01)

(58) Field of Classification Search
CPC ........ A01N 27/00; A01N 3/02; A23B 27/152; A23L 3/34; A23L 3/3409; A23L 3/3445; B65D 81/24; C08B 37/0015; C08J 7/047; C09D 105/16; C09D 103/02
USPC ..... 525/63, 54.2, 64, 55, 231, 240; 442/334, 442/351, 401; 428/77, 220, 34.2, 34.3, 428/34.7, 35.7; 252/399; 426/323; 526/238.22

See application file for complete search history.

(56) References Cited

U.S. PATENT DOCUMENTS

| | | |
|---|---|---|
| 3,493,362 A | 2/1970 | Ferm |
| 3,661,549 A | 5/1972 | Freytag et al. |
| 3,676,102 A | 7/1972 | Clark et al. |
| 3,810,749 A | 5/1974 | Young |
| 3,840,448 A | 10/1974 | Osborn et al. |
| 3,879,188 A | 4/1975 | Fritz et al. |
| 3,885,950 A | 5/1975 | Ehrig et al. |
| 3,940,667 A | 2/1976 | Pearce |
| 3,943,103 A | 3/1976 | Borden et al. |
| 4,181,752 A | 1/1980 | Martens et al. |
| 4,356,115 A | 10/1982 | Shibanai et al. |
| 4,432,802 A | 2/1984 | Harata et al. |
| 4,438,106 A | 3/1984 | Wagu et al. |
| 4,547,572 A | 10/1985 | Fenyvesi et al. |
| 4,575,548 A | 3/1986 | Ueda et al. |
| 4,636,343 A | 1/1987 | Shibanai |
| 4,675,395 A | 6/1987 | Fukazawa et al. |
| 4,677,177 A | 6/1987 | Shibanai et al. |
| 4,681,934 A | 7/1987 | Shibanai et al. |
| 4,711,936 A | 12/1987 | Shibanai et al. |
| 4,722,815 A | 2/1988 | Shibanai |
| 4,725,633 A | 2/1988 | Shibanai |
| 4,725,657 A | 2/1988 | Shibanai |
| 4,728,510 A | 3/1988 | Shibanai et al. |
| 4,732,758 A | 3/1988 | Hurion et al. |
| 4,732,759 A | 3/1988 | Shibanai et al. |
| 4,735,979 A | 4/1988 | Beers et al. |
| 4,769,242 A | 9/1988 | Shibanai |
| 4,772,291 A | 9/1988 | Shibanai et al. |
| 4,833,674 A | 5/1989 | Takai et al. |
| 4,834,985 A | 5/1989 | Elger et al. |
| 4,847,151 A | 7/1989 | Ichiro |

(Continued)

FOREIGN PATENT DOCUMENTS

| | | |
|---|---|---|
| AU | 2011268471 | 3/2012 |
| CA | 2692211 | 9/2011 |

(Continued)

OTHER PUBLICATIONS

Lyondell Chemical Company, "Alathon M6210 High Density Polyethylene", Date Unknown.*
Crowe et al., "Chemistry for the Biosciences: Essential Concepts", Oxford University Press, Oxford, 2014.*
Hotchkiss et al. "Release of 1-Methylcyclopropene from Heat-Pressed Polymer Films", Journal of Food Science, 72. 5 (2007).*
PCT International Search Report and Written Opinion from International Application No. PCT/US2010/060067, corresponding to U.S. Appl. No. 12/967,226, mailed Apr. 28, 2011 (10 pages).
"Affinity™ KC 8852G, Polyolefin Plastomer", Form No. 400-00050072en, Rev: Jun. 3, 2009, The Dow Chemical Company, www.dowplastics.com (2009) (2 pgs.).
"Affinity™ PF 1140G, Polyolefin Plastomer", Form No. 400-00071417en, Rev. 2009-06-03, The Dow Chemical Company, www.dowplastics.com (2009) (3 pgs.).

(Continued)

Primary Examiner — Lee E Sanderson
(74) Attorney, Agent, or Firm — Kagan Binder, PLLC

(57) ABSTRACT

Thermoplastic polyolefin polymer compositions, polymer chips, fibers, woven or nonwoven fabrics, films, closures, and laminates include a polymer and cyclodextrin compound with a volatile maturation inhibitor or an olefinic ethylene receptor antagonist in respiring produce materials. The polymer composition can also include a cyclodextrin-modified polymer or a substituted cyclodextrin. Olefinic ethylene inhibitors can be formed in the cyclodextrin composition, wherein the cyclodextrin releases the olefinic inhibitor composition when used in produce packaging materials. Coating compositions can also be made. The inhibitor is introduced into the materials and is released under controlled conditions of humidity. Upon release, the olefinic inhibitor blocks ethylene receptor sites on proteins that control maturation and can produce an extended period during which the produce does not substantially complete maturation or ripening to a degree leading to spoilage.

10 Claims, No Drawings

(56) References Cited

U.S. PATENT DOCUMENTS

| | | |
|---|---|---|
| 4,871,541 A | 10/1989 | Shibanai |
| 4,883,674 A | 11/1989 | Fan |
| 5,070,081 A | 12/1991 | Majid et al. |
| 5,078,920 A | 1/1992 | Maza |
| 5,100,462 A | 3/1992 | Sisler et al. |
| 5,183,655 A | 2/1993 | Stanislowski et al. |
| 5,360,899 A | 11/1994 | Nussstein et al. |
| 5,474,698 A | 12/1995 | Rolando et al. |
| 5,518,988 A | 5/1996 | Sisler et al. |
| 5,723,714 A | 3/1998 | Binger |
| 5,730,311 A | 3/1998 | Curtis |
| 5,760,129 A | 6/1998 | Lau |
| 5,776,842 A | 7/1998 | Wood et al. |
| 5,832,699 A | 11/1998 | Zobel |
| 6,017,849 A | 1/2000 | Daly et al. |
| 6,092,761 A | 7/2000 | Mushaben |
| 6,162,533 A | 12/2000 | Onozawa et al. |
| 6,194,350 B1 | 2/2001 | Sisler |
| 6,206,947 B1 | 3/2001 | Evans et al. |
| 6,232,365 B1 | 5/2001 | Weiss et al. |
| 6,271,127 B1 | 8/2001 | Liu et al. |
| 6,296,923 B1 | 10/2001 | Zobel |
| 6,313,068 B1 | 11/2001 | Daly et al. |
| 6,358,670 B1 | 3/2002 | Wong et al. |
| 6,365,549 B2 | 4/2002 | Sisler |
| 6,426,319 B1 | 7/2002 | Kostansek |
| 6,444,619 B1 | 9/2002 | Kostansek |
| 6,451,065 B2 | 9/2002 | Trinh et al. |
| 6,452,060 B2 | 9/2002 | Jacobson |
| 6,548,132 B1 | 4/2003 | Clarke et al. |
| 6,548,448 B2* | 4/2003 | Kostansek ................ 504/193 |
| 6,613,703 B1 | 9/2003 | Yahiaoui et al. |
| 6,709,746 B2 | 3/2004 | Wood et al. |
| 6,720,476 B2 | 4/2004 | Clendennen et al. |
| 6,762,153 B2 | 7/2004 | Kostansek et al. |
| 6,766,612 B1 | 7/2004 | Liu |
| 6,770,600 B1 | 8/2004 | Lamola et al. |
| 6,831,116 B2 | 12/2004 | Bitler et al. |
| 6,852,904 B2 | 2/2005 | Sun et al. |
| 6,953,540 B2 | 10/2005 | Chong et al. |
| 6,987,099 B2 | 1/2006 | Trinh et al. |
| 7,001,661 B2 | 2/2006 | Beaverson et al. |
| 7,019,073 B2 | 3/2006 | Etherton et al. |
| 7,041,625 B2 | 5/2006 | Jacobson et al. |
| 7,157,411 B2 | 1/2007 | Rohde et al. |
| 7,169,451 B2 | 1/2007 | Clarke et al. |
| 7,182,941 B2 | 2/2007 | Trinh et al. |
| 7,531,471 B2 | 5/2009 | Quincy, III |
| 7,549,396 B2 | 6/2009 | Hurwitz et al. |
| 7,569,160 B2 | 8/2009 | Oldenzijl et al. |
| 7,601,374 B2 | 10/2009 | Clarke |
| 7,629,042 B2 | 12/2009 | Jones et al. |
| 7,637,054 B2 | 12/2009 | Alfrey et al. |
| 7,758,885 B2 | 7/2010 | Myhra |
| 7,799,885 B2 | 9/2010 | Shustack et al. |
| 7,943,549 B2 | 5/2011 | Pierce et al. |
| 7,997,026 B2 | 8/2011 | Webster et al. |
| 8,093,430 B2 | 1/2012 | Sisler |
| 8,168,860 B2 | 5/2012 | Rosichan et al. |
| 8,247,459 B2 | 8/2012 | Kostansek |
| 8,314,051 B2 | 11/2012 | Yoo |
| 8,461,086 B2 | 6/2013 | Chang et al. |
| 8,481,127 B2 | 7/2013 | Wood et al. |
| 2001/0019995 A1 | 9/2001 | Sisler |
| 2001/0044392 A1 | 11/2001 | Trinh et al. |
| 2002/0007055 A1 | 1/2002 | Uchiyama et al. |
| 2002/0012759 A1 | 1/2002 | Asayama et al. |
| 2002/0043730 A1* | 4/2002 | Chong ................ B01J 13/02 264/4.1 |
| 2002/0058592 A1 | 5/2002 | Kostansek |
| 2002/0061822 A1 | 5/2002 | Kostansek |
| 2002/0129404 A1 | 9/2002 | Clendennen et al. |
| 2002/0198107 A1 | 12/2002 | Kostansek |
| 2003/0068295 A1 | 4/2003 | Rohde et al. |
| 2003/0100450 A1 | 5/2003 | Kostansek et al. |
| 2003/0170570 A1 | 9/2003 | Vander Aa et al. |
| 2003/0220201 A1 | 11/2003 | Kostansek et al. |
| 2004/0072694 A1 | 4/2004 | Jacobson et al. |
| 2004/0192554 A1 | 9/2004 | Kashimura et al. |
| 2005/0043482 A1* | 2/2005 | Etherton et al. ............ 525/63 |
| 2005/0250649 A1 | 11/2005 | Jacobson et al. |
| 2005/0260907 A1 | 11/2005 | Chang et al. |
| 2005/0261131 A1 | 11/2005 | Basel et al. |
| 2005/0261132 A1 | 11/2005 | Kostansek et al. |
| 2006/0135369 A1 | 6/2006 | Beltran |
| 2006/0154822 A1 | 7/2006 | Toivonen et al. |
| 2006/0160704 A1 | 7/2006 | Basel et al. |
| 2007/0003741 A1 | 1/2007 | Sakurai et al. |
| 2007/0105722 A1 | 5/2007 | Basel et al. |
| 2007/0110791 A1 | 5/2007 | Myhra |
| 2007/0196319 A1 | 8/2007 | Alfrey et al. |
| 2007/0265166 A1 | 11/2007 | Bardella et al. |
| 2007/0265167 A1 | 11/2007 | Edgington et al. |
| 2008/0092613 A1 | 4/2008 | Alfrey et al. |
| 2008/0214399 A1 | 9/2008 | Belkind et al. |
| 2008/0236038 A1 | 10/2008 | Pierce et al. |
| 2008/0294132 A1 | 11/2008 | Tan et al. |
| 2008/0310991 A1 | 12/2008 | Webster et al. |
| 2009/0035380 A1 | 2/2009 | Kostansek |
| 2009/0077684 A1 | 3/2009 | Gallie et al. |
| 2009/0088323 A1 | 4/2009 | Basel et al. |
| 2009/0124504 A1 | 5/2009 | Sisler |
| 2009/0186762 A1 | 7/2009 | Rademacher et al. |
| 2009/0220739 A1 | 9/2009 | Chougule |
| 2009/0230350 A1 | 9/2009 | Jacobson et al. |
| 2009/0245876 A1 | 10/2009 | Tohata et al. |
| 2010/0076242 A1 | 3/2010 | Yoo |
| 2011/0033540 A1 | 2/2011 | Daniloff et al. |
| 2011/0143004 A1 | 6/2011 | Wood et al. |
| 2012/0004108 A1 | 1/2012 | Zhen |
| 2012/0107459 A1 | 5/2012 | Wood et al. |
| 2013/0029058 A1 | 1/2013 | Wood et al. |
| 2014/0011679 A1 | 1/2014 | Mir |

FOREIGN PATENT DOCUMENTS

| | | |
|---|---|---|
| CN | 1371603 A | 10/2002 |
| CN | 1703955 | 12/2005 |
| CN | 101104665 | 1/2008 |
| CN | 101297659 | 11/2008 |
| CN | 201501603 | 6/2010 |
| CN | 101990937 | 3/2011 |
| CN | 102047946 | 5/2011 |
| CN | 102119719 | 7/2011 |
| CN | 102532611 | 7/2012 |
| DE | 4035378 | 5/1992 |
| EP | 1 236 397 A2 | 9/2002 |
| EP | 1559746 | 8/2005 |
| EP | 1593306 | 11/2005 |
| EP | 2383614 A2 | 11/2011 |
| EP | 2389814 A1 | 11/2011 |
| GB | 1119545 A | 7/1968 |
| GB | 2492284 | 12/2012 |
| GB | 2491424 | 4/2013 |
| JP | 06118719 A | 4/1994 |
| JP | 8-100027 A | 4/1996 |
| JP | 2002174925 A | 6/2002 |
| JP | 2002281894 A | 10/2002 |
| JP | 2002-356401 A | 12/2002 |
| JP | 2005258333 A | 9/2005 |
| JP | 2007-256773 A | 10/2007 |
| JP | 2013513719 | 4/2013 |
| NZ | 514235 | 7/2002 |
| NZ | 514236 | 1/2003 |
| NZ | 521818 | 3/2004 |
| NZ | 524289 | 7/2004 |
| NZ | 539684 | 12/2006 |
| NZ | 551211 | 12/2008 |
| NZ | 554976 | 3/2009 |
| NZ | 563094 | 4/2009 |
| NZ | 568774 | 12/2009 |
| NZ | 578429 | 12/2011 |
| TW | 201311803 | 3/2013 |
| WO | WO-0113968 | 3/2001 |

(56) References Cited

FOREIGN PATENT DOCUMENTS

| | | |
|---|---|---|
| WO | WO 02/20668 A2 | 3/2002 |
| WO | WO-2006046254 | 5/2006 |
| WO | WO-2006072180 | 7/2006 |
| WO | WO-2008089140 | 7/2008 |
| WO | WO 2008089140 A1 * | 7/2008 |
| WO | WO-2011081877 | 7/2011 |
| WO | WO-2012134539 | 10/2012 |

OTHER PUBLICATIONS

"Basell—Polybutene-1 PB 0300M—Polybutene-1", http://basell.com/portal/binary/com.vignette.vps.basell.productgrade.ProductGradeFileDisplay?id+27d684b40c337010VgnVC . . . (2 pgs.) (Jul. 18, 2006).

"Canadian Office Actions mailed Feb. 9, 2011 and Nov. 2, 2010 in co-pending Canadian Patent Application No. 2,692,211", (3 pgs.).

"DuPont™ FusabondR P MD353D", DuPont Packaging & Industrial Polymers, http://www.dupont.com (2 pgs.) (Jun. 2005).

"Ethylbloc Registration No. 71297-1 and Ethylbloc Sachet Registration No. 71297-5", Firm No. 71297, Agro Fresh Inc., Philadelphia, PA, http://ppis.ceris.purdue.edu/htbin/rnamset.com (3 pgs.) (Feb. 2, 2011).

"ExxonMobil™ LDPE LGA 105, Low Density Polyethylene Resin", ExxonMobil Chemical, www.exxonmobilpe.com (2 pgs.) (Nov. 6, 2009).

"ExxonMobil™ PP3155: Polypropylene Homopolymer ExxonMobil Chemical", IDES Prospector, IDES—The Plastics Web, www.ides.com (1 pg.) (Nov. 6, 2009).

"Fresh As the Day It Was Harvested—Luscious Fruit Thanks to Cyclodextrins", Wacker Chemie AG, www.wacker.com, No. 5 (9 pgs.) (May 2009).

"Fusabond® P MD411D", IDES Prospector, www.ides.com (1 pg.) (Nov. 6, 2009).

"Integrate™ NE542013, Functinalized Polyolefin, Melt Index 13, Density 0.943", Equistar, Lyondell Chemical Company, Houston, Texas, http://www.Lyondell.com (1 pg.) (Mar. 2006).

"PC Code 224459, Chemical Name Cyclopropene, 1-methyl-", Firm No. 71297, Agro Fresh Inc., http://ppis.ceris.purdue.edu/htbin/cnamlist.com (2 pgs.) (Feb. 11, 2011).

"Trademark Search for ETHYLBLOC", http://tess2.uspto.gov/bin/showfield?f+doc&state+4005:6v38ie.2.1 (2 pgs.) (Feb. 11, 2011).

Amiel, "Cyclodextrin polymers and drug delivery", Systemes Polymeres Complexes, ICMPE, J. Drug Del. Sci. Tech. (21 pgs.) (2004).

Burg et al., "Molecular Requirements for the Biological Activity of Ethylene", Plant Physiol. 42:144-152 (1967).

Cheng et al., "Synthesis of Linear, β-Cyclodextrin-Based Polymers and Their Camptothecin Conjugates", Bioconjugate Chem., 14:1007-1017 (2003).

Hotchkiss et al., "Release of 1-Methylcyclopropene from Heat-Pressed Polymer Films", Journal of Food Science, 72(5):E330-E334 (2007).

Hwang et al., "Effect of Structure of β-Cyclodextrin-Containing Polymers on Gene Delivery", Bioconjugate Chem., 12:280-290 (2001).

Macnish et al., "A simple sustained release device for the ethylene binding inhibitor 1-methylcyclopropene", Institute of BioScience and Technology, Cranfield University at Silsoe, Befordshire MK45 4DT, UK (50 pgs.) (date unknown).

Neoh et al., "Dissociation characteristics of the inclusion complex of cyclomaltohexaose (α-cyclodextrin) with 1-methylcyclopropene in response to stepwise rising relative humidity", Carbohydrate Research, 345:2085-2089 (2010).

Neoh et al., "Kinetics of Molecular Encapsulation of 1-Methylcyclopropene into a-Cyclodextrin", J. Agric. Food Chem., 55:11020-11026 (2007).

Orellana, "Ninesigma—Request # 50882-1—Entrapping Gases for Agricultural Formulations", NineSigma, Inc., www.ninesigma.com (2 pgs.) (2009).

Pirrung, ""A new idea for how anti-aging products delay ripening of fruit and wilting of flowers"", www.physorg.com/news128959515.html (2 pgs.) (May 2, 2008).

Sisler et al., "Competition of cyclooctenes and cyclooctadienes for ethylene binding and activity in plants", Plant Growth Regulation, 9:157-164 (1990).

Sisler et al., "Competition of unsaturated compounds with ethylene for binding and action in plants", Plant Growth Regulation, 7:181-191 (1988).

Sisler et al., "Inhibitors of ethylene responses in plants at the receptor level: Recent developments", Physiologia Plantarum, 100:577-582 (1997).

Wooster, Jeffrey J., "Extending the Shelf-life of Fresh-cut Produce (Including the Many Advantages of Affinity Polyolefin Plastomers)", The Dow Chemical Company 2010, 1-16.

Ambaw, Alemayehu et al., "Modeling of Diffusion-Adsorption Kinetics of 1-Methylcyclopropene (1-MCP) in Apple Fruit and Non-Target Materials in Storage Rooms", 2010, 1-5.

"1-Methylcyclopropene; Amendment to an Exemption from the Requirement of a Tolerance", Federal Register / vol. 73, No. 69 / Wednesday, Apr. 9, 2008 /Rules and Regulations 2008, 9147-19150.

"FAO Specifications and Evaluations for Agricultural Pesticides 1-Methylcyclopropene", 2008, 1-26.

Utto, Weerawate, "Mathematical Modeling of Active Packaging Systems for Horticultural Products", 2008, 1-363.

Watkins, Christopher B., "Overview of 1-Methylcyclopropene Trials and Uses for Edible Horticultural Crops", 2008, 1-19.

Thoden Van Velzen, E.U., "Packaging for fresh convenience food", Agrotechnology & Food Sciences Group—Wageningenur, 2008, 1-29.

Reid, Michael S. et al., "Use of 1-Methylcyclopropene", in Ornamentals: Carnations as a Model System for Understanding Mode of Action Hort Science vol. 43(1) Feb. 2008, 95-98.

Nanthachai, Nunchanok et al., "Absorption of 1-MCP by fresh produce", Postharvest Biology and Technology 43 (2007), 291-297.

Lee, Younsuk S. et al., "Development of a 1-Methylcyclopropene (1-MCP) Sachet Release System", Journal of Food Science—vol. 71, Nr. 1, 2006 Section C: Food Chemistry & Toxicology 2006, C1-C6.

Husken, Debby, "Hydrophilic Segmented Block Copolymers Based on Poly(Ethylene Oxide)", 2006, 1-199.

Watkins, Chris B., "The use of 1-methylcyclopropene (1-MCP) on fruits and vegetables", Biotechnology Advances 24 (2006), 389-409.

Watkins, Chris B. et al., "A summary of physiological processes or disorders in fruits, vegetables and ornamental products that are delayed or decreased, increased, or unaffected by application of 1-methycyclopropene (1-MCP)", 2005 , 1-20.

"Conclusion regarding the peer review of the pesticide risk assessment of the active substance 1-methylcyclopropene", EFSA Scientific Report (2005), 1-46.

Macnish, Andrew J. et al., "A simple sustained release device for the ethylene binding inhibitor 1-methylcyclopropene", 2004, 1-50.

Blankenship, Sylvia M. et al., "1-Methylcyclopropene: a review", Postharvest Biology and Technology 28 2003, 1-25.

Sisler, Edward C. et al., "Compounds controlling the ethylene receptor", Bot. Bull. Acad. Sin. 40:1_7 http://ejournal.sinica.edu.tw/bbas/content/1999/1/bot41-01.html 1999, 1-13.

Jiang, Yueming et al., "Extension of the shelf life of banana fruit by 1-methylcyclopropene in combination with polyethylene bags", Postharvest Biology and Technology 16, 1999, 187-193.

Denter, E. et al., "Surface Modification of Synthetic and Natural Fibres by Fixation of Cyclodextrin Derivatives", Journal of Inclusion Phenomena and Molecular Recognition in Chemistry 25, 197-202, 1996.

Zhao, Xiao-Bin et al., "Synthesis and charcterization of polymer-immobilized β-cyclodextrin with an inclusion recognition functionality", Elsevier Science B.V., Reactive Polymers 24 (1994) 9-16.

Shkolnik, S. et al., "Radiation-Induced Grafting of Sulfonates on Polyethylene", Journal of Applied Polymer Science, vol. 27, 2189-2196(1982).

Chanda, M. and Roy, S., Plastics Technology Handbook, 4th ed., CRC Press, at 1-34 (1 page).

(56) References Cited

OTHER PUBLICATIONS

"1 Extension Admission", for the use of "Smartfresh" http://www.ctb.agro.nl/ctb_files/12522_08.html (61 pages).
Deell, J. et al., "1-methylcyclopropene influence 'Empire' and 'Delicious' apple quality during long-term commercial storage", HortTechnology, Jan.-Mar. 2007, 17(1), 46-51.
"AU First Examiner Report Received", from AU Application No. 2010337146, mailed Nov. 9, 2012, (pp. 1-3) Including English translation.
"Combined Search and Exam Report", for United Kingdom Application No. 1218077.4, mailed Oct. 23, 2012, (6 pages).
"Combined Search and Examination Report under Sections 17 and 18(3)", from GB Application No. GB1119545.0, corresponding to U.S. Appl. No. 13/287,944, mailed Jan. 12, 2012, (pp. 1-6).
"Final Office Action", mailed Nov. 8, 2012 in co-pending U.S. Appl. No. 13/287,944, "Cyclodextrin Compositions, Articles, and Methods ," (22 pages).
"Final Office Action", mailed Apr. 26, 2013, in co-pending U.S. Appl. No. 12/967,226, (11 pages).
"First Exam Report", for Australian Application 2012203412, mailed Mar. 22, 2013 (3 pages).
"First Examiner Report Received", for Australia Application No. 2011268471, corresponding to U.S. Appl. No. 61/468,041, mailed Feb. 6, 2012, (1 page) English translation.
"First Office Action", for Chinese Application No. 201080060634.6, mailed May 29, 2013 (10 pages).
"First Office Action", mailed Nov. 2, 2010, in co-pending Canadian Patent Application No. 2,692,211. (2 pages).
"Non-Final Office Action", from U.S. Appl. No. 13/896,803, mailed Aug. 15, 2013, 30 pages.
"Non-Final Office Action", mailed Apr. 27, 2012 in co-pending U.S. Appl. No. 13/287,944, "Cyclodextrin Compositions, Articles, and Methods ," (26 pages).
"Notice of Allowance", for U.S. Appl. No. 13/287,944, mailed Feb. 8, 2013, 12 pages.
"Notice of Allowance", from CA Application No. 2,692,211, corresponding to U.S. Appl. No. 61/286,177, mailed Mar. 23, 2011, (pp. 1).
"Notice of Allowance", from U.S. Appl. No. 13/574,287, mailed May 14, 2013, 14 pages.
"Notice of Allowance", mailed Sep. 18, 2012, in Australian Application Serial No. 2011268471, (1 page).
"Office Action", from GB Application No. 1218077.4, corresponding to U.S. Appl. No. 13/574,287, mailed Oct. 23, 2012, (6 pages).
"Office action Received", for United Kingdom Application No. 1119545.0, corresponding to U.S. Appl. No. 61/468,041, mailed Sep. 11, 2012 (2 pages).
"Paraffin wax", http://www.chemicalbook.com/ChemicalProductProperty_EN_CB2854418.htm, 2010, 2 pages.
"PCT International Search Report and Written Opinion", from International Application No. PCT/US2011/057017, corresponding to U.S. Appl. No. 13/574,287, mailed Jan. 30, 2012, (3 pages).
"PCT Notification Concerning Transmittal of International Preliminary Report on Patentability", from International Application No. PCT/US2010/060067, corresponding to U.S., mailed Jun. 28, 2012, pp. 1-7.
Wood, Will, "Polyolefin Grafted Cyclodextrin", 14th International Cyclodextrin Symposium, Kyoto, JP, May 8, 2008, 6 pages.
"Regulatory Note REG2004-07", Pest Management Regulatory Agency, 2004. 1- Methylcyclopropene, Regulatory note Reg 2004-07, PMRA, Health Canada, Ottawa, Ont., pp. 1-56.
"Response to First Canadian Office Action", mailed Nov. 2, 2010, in co-pending Canadian Patent Application No. 2,692,211, Filed Dec. 22, 2010. (24 pages).
"Response to First Examiner's Report", for Australia Application No. 2010337146, corresponding to U.S. Appl. No. 12/967,226, mailed Jan. 25, 2013, (2 Pages).
"Response to First Examiner's Report", for Australia Application No. 2011268471, corresponding to U.S. Appl. No. 61/468,041, mailed Feb. 28, 2012, (20 pages).
"Response to Non-Final Office Action", mailed Nov. 26, 2012, in co-pending U.S. Appl. No. 12/967,226, filed with USPTO Feb. 26, 2013 (16 pages).
"Response to Office Action", from GB Application No. 1119545.0, corresponding to U.S. Appl. No. 13/574,287, mailed Jun. 6, 2012, (11 pages).
"Response to Office Action", from GB Application No. 1119545.0, corresponding to U.S. Appl. No. 13/574,287, mailed Oct. 9, 2012 (13 pages).
"Response to Office Action", from GB Application No. 1218077.4, corresponding to U.S. Appl. No. 13/574,287, mailed Apr. 23, 2013 (14 pages).
"Response to Second Canadian Office Action", mailed Feb. 9, 2011, in co-pending Canadian Patent Application No. 2,692,211. Filed Feb. 22, 2011 (13 pages).
"Response to United Kingdom's Office Action", dated Jan. 12, 2012 Filed in the United Kingdom Patent Office on Feb. 13, 2012 for United Kingdom's Patent Application No. 1119545.0 corresponding to U.S. Appl. Nos. 61/468,041, (18 pages).
"Second Examination Report", for Australia Application No. 2010337146, corresponding to U.S. Appl. No. 12/967,226, mailed Feb. 19, 2013, (3 Pages).
"UK Office Action Received", Citation for United Kingdom Application No. 1119545.0, corresponding to U.S. Appl. No. 61/468,041, mailed Apr. 4, 2012, Including English translation, 2 pgs.
First Office Action dated May 29, 2013 in Chinese Application No. 201080060634.6.
Second Office Action dated Jan. 3, 2014 in Chinese Application No. 201080060634.6.
Official Action mailed Nov. 20, 2013 in Mexican Application No. MX/a/2012/006797.
Official Action mailed Feb. 7, 2014 in Mexican Application No. MX/a/2012/006797.
Notice of Acceptance dated Aug. 14, 2013 in Australian Application No. 2010337146.
The First Examination Report dated Jun. 6, 2014 in related New Zealand Application No. 616943.
Maatz, Gero et al. "Cyclodextrin-induced host-guest effects of classically prepared poly(NIPAM) bearing azo-dye end groups" Beilstein Journal of Organic Chemistry. 2012, 8, 1929-1935.
Regiert, Marlies et al. "Light-Stable Vitamin E by Inclusion in γ-Cyclodextrin" Sun Screens & UV Protection, Cosmetic Science Technology, 2006, p. 95.
Aug. 26, 2014 Office Action in Japanese Application No. 2012-544678. Translation included.
Aug. 26, 2014 Office Action in European Application No. 11785170.9.
Sep. 11, 2014 Office Action in Korean Application No. 10-2013-7028386. Translation included.
Sep. 12, 2014 Examination Report in Canadian Application No. 2,831,213.
Oct. 5, 2014 Translation of Notification of Defects in Israeli Application No. 228558.
Oct. 27, 2014 Office Action in Russian Application No. 2012129253. Translation included.
Office Action dated Mar. 5, 2015 in Russian Patent Application No. 2012129253 and English Translation, 8 pages.
Office Action dated Mar. 19, 2015 in European Patent Application No. 10795543.7, 3 pages.
The First Office Action dated Aug. 3, 2015 in Chinese Patent Application No. 201410461847X, with English translation.
Examination Report dated Mar. 4, 2016, from European Application No. 10795543.7.
Final Official Action dated May 20, 2015 in connection with Japanese Patent Application No. 2012-544678, with English Translation.

* cited by examiner

MATURATION OR RIPENING INHIBITOR RELEASE FROM POLYMER, FIBER, FILM, SHEET OR PACKAGING

CROSS REFERENCE TO RELATED APPLICATION

This application claims the benefit of U.S. Provisional Patent Application Ser. No. 61/286,177, filed Dec. 14, 2009, which application is hereby incorporated by reference in its entirety.

FIELD OF THE INVENTION

The disclosure relates to methods of extending the useful life of produce or produce materials. The invention further relates to the use of packaging materials that have a capacity of reducing produce maturation, extending the lifetime of produce, and preventing produce spoilage using an olefinic antagonist or inhibitor of the ethylene receptor sites in growth and ripening regulator proteins. The disclosure relates to thermoplastic polymer compositions, typically vinyl polymers or polyolefin compositions that can release the antagonist or inhibitor. These compositions or polymer materials can be used as fiber, woven and nonwoven fabric, film, polymer webs of various thickness, rigid or semi rigid sheets, chips, as a coating or barrier coating or in other useful polymer forms for making packaging materials, packages, package inserts and other packaging technology.

BACKGROUND

The shelf life of produce or produce materials, including whole plants plant parts thereof including fruits, vegetables, tubers, bulbs, cut flowers and other active respiring plants or plant materials, is typically determined, at least in part, by the amount of an ethylene hormone generated by the respiring plant material. Ethylene is a known plant ripening or maturation hormone. At any substantial concentration of ethylene in and around the plant material, the maturation of the plant is initiated, maintained or accelerated, depending on concentration. See, Burg et al., Plant Physiol. (1967) 42 144-152 and generally Fritz et al. U.S. Pat. No. 3,879,188. Many attempts have been made to either remove ethylene from the ambient package atmosphere surrounding the produce or to remove ethylene from the storage environment in an attempt to increase shelf life. Reduced ethylene concentration is understood to be achieved through a decrease in the stimulus of a specific ethylene receptor in plants. Many compounds other than ethylene interact with this receptor: some mimic the action of ethylene; others prevent ethylene from binding and thereby counteract its action.

Many compounds that act as an antagonist or inhibitor block the action of ethylene by binding to the ethylene binding site. These compounds may be used to counteract ethylene action. Unfortunately, they often diffuse from the binding site over a period of several hours leading to a reduction in inhibition. See E. Sisler and C. Wood, Plant Growth Reg. 7, 181-191 (1988). Therefore, a problem with such compounds is that exposure must be continuous if the effect is to last for more than a few hours. Cyclopentadiene has been shown to be an effective blocking agent for ethylene binding. See E. Sisler et al., Plant Growth Reg. 9, 157-164 (1990). Methods of combating the ethylene response in plants with diazocyclopentadiene and derivatives thereof are disclosed in U.S. Pat. No. 5,100,462 to Sisler et al. U.S. Pat. No. 5,518,988 to Sisler et al. describes the use of cyclopropenes having a $C_{1-4}$ alkyl group to block the action of ethylene.

A preferred olefinic antagonist or inhibitor of receptor sites or ethylene generation in produce is 1-methylcyclopropene, derivatives and analogs thereof have also been tried as an antagonist or inhibitor for the generation of ethylene from respiring plant or produce material. 1-methyl-cyclopropene (1-MCP), 1-butene and other olefins have been shown to have at least some measurable activity for inhibiting ethylene generation and thus extending shelf life. We find that 1-butane is a good model for 1-MCP activity A number of proposals have been made for the method of producing and releasing 1-MCP to inhibit ethylene release and as a result slowing maturation and maintaining the quality of plant materials. Currently 1-MCP is dispensed directly from a pressure vessel or by the release of 1-MCP from a sachet containing complexed 1-MCP. In these technologies, 1-MCP is released from a point source which causes a concentration of gradient within the storage chamber thus resulting in a variation in maturation inhibition wherein some produce has an extended life time where other produce exposed to a lesser concentration 1-MCP tends to have less inhibition of ethylene and has a reduced shelf life.

Notwithstanding these efforts, there remains a substantial need in the art for improved plant maturation and degradation prevention.

BRIEF DESCRIPTION OF THE INVENTION

The invention relates to thermoplastic material that can contain a compatible cyclodextrin composition such that the cyclodextrin composition contains an effective amount and a controlled release amount of an olefinic inhibitor of ethylene generation in produce. The thermoplastic material can be made with a cyclodextrin pendant group or a cyclodextrin in the polymer backbone. The thermoplastic material can be used as a material in the formation of produce containers, packaging or packaging components or inserts that can generate a uniform ethylene inhibiting amount of the olefinic inhibitor such that the produce within the container has a consistent quality and extended useful life time. The compositions of the invention can also comprise a coating composition that can form a layer on the substrate. The layer containing the cyclodextrin with the inhibitor compound in the central core of the cyclodextrin is an effective source of the inhibitor.

The invention contemplates a thermoplastic composition comprising a compatible or pendant cyclodextrin material and held within the cyclodextrin material an effective amount of the olefinic inhibitor of ethylene generation in produce. This thermoplastic material can be formed into or coated onto fiber, film, sheet or rigid or semi-rigid containers that can release olefinic inhibitor into an enclosed volume within a packaging structure such that the produce material has an extended or more useful life time. The invention also contemplates that the cyclodextrin compound can be a substituted cyclodextrin containing the olefinic inhibitor, a polymer material having grafted cyclodextrin containing the olefinic inhibitor or a polymer composition such that the cyclodextrin compound is formed in the polymer chain or backbone such that the cyclodextrin contains the olefin inhibitor.

The invention also contemplates that the thermoplastic composition containing this cyclodextrin can be manufactured with a unique method such that the cyclodextrin and thermoplastic material is formed under conditions having reduced water content such that the polymer absorbs substantial quantities of the olefinic inhibitor allowing the cyclodextrin material to form an inclusion complex with the olefinic inhibitor. Once an inclusion complex is formed with the cyclodextrin material, the thermoplastic material can be formed into or coated onto packaging material and the packaging material can be used to package respiring produce material. The produce material is packaged within the thermoplastic packaging and is contacted with an appropriate and activating amount of water such that the cyclodextrin releases the olefinic material at sufficient concentration to inhibit produce material maturation. The inhibitor material is also released from the packaging by exposing the packaging to a controlled level of humidity. The humidity can be controlled by forming the packaging from a polymer containing the cyclodextrin compound and the inhibitor compound. During distribution and storage when the packaged produce material storage temperature is low (for example, between about 2° C. to about 14° C.), the humidity in the enclosed volume around the produce will be high (for example, between about 70% to about 100% relative humidity) due to normal water loss from produce respiration into the enclosed package volume. Parenthetically, the gaseous products of respiration (i.e. carbon dioxide and water) are the reactants in the process of photosynthesis. The increase in humidity within the enclosed volume of the package is sufficient to release the inhibitor. Alternatively, the internal humidity of the packaging can be adjusted by the addition of water prior to sealing the produce package to release the inhibitor. Relative humidity can be controlled by adding moisture (water mist, spray or steam) to air by humidifiers during packaging.

Further, a typical packaging material for produce or produce material can be made from conventional packaging materials and can contain the produce with a package insert comprising a material of the invention that can release the inhibitor compound by the increase or addition of a controlled level of humidity.

The invention relates to a thermoplastic polymer containing a cyclodextrin compound having an olefinic inhibitor of ethylene generation. The cyclodextrin compound containing inhibitor material can be used in bulk polymer or as a coating. In the polymer the cyclodextrin compound can be grafted onto the polymer or can be formed into the polymer backbone. A second aspect of the invention involves a thermoplastic composition comprising a thermoplastic polymer and a derivative of the cyclodextrin compound with the olefinic inhibitor of ethylene generation in the central pore of the cyclodextrin. A further aspect of the invention is a film, a fiber, a sheet, a rigid or a semi-rigid packaging material, a woven or non-woven fabric manufactured from a polymer composition of the invention. A further aspect of the invention is a method of packaging produce for the purpose of extending its useful life or reducing maturation or ripening by packaging produce material in a package that comprises of at least some portion of the package manufactured from the polymer compositions of the invention. In such a method, the package can comprise a film or rigid or semi-rigid packaging material forming an enclosure containing the produce. Alternatively, the packaging material can be made from conventional polymer materials and can enclose the produce that is packaged with a package insert comprising the polymer materials of the invention. A still further aspect of the invention is the method of manufacturing the polymer composition containing the cyclodextrin and the olefinic inhibitor of ethylene generation involving a careful and sufficiently anhydrous introduction of the inhibitor into the central pore of the cyclodextrin molecule that is contained in the polymer material. A further aspect of the invention is the controlled introduction of the inhibitor into the cyclodextrin central core under conditions of controlled temperature, humidity and pressure. Lastly, an aspect of the invention is a method of controlled release of the olefinic inhibitor of ethylene generation from the polymer compositions of the invention using a careful humidity modulated release, previously described, of the inhibitor from the polymer materials. We have found that the inhibitor olefin can be controllably released from the polymer compositions of the invention by carefully maintaining a specific humidity within the packaging material such that the level of humidity is proportional to the amount of ethylene inhibitor released by the polymer materials in the packaging structures or in the method of the packaging.

For the purpose of this disclosure, the term "cyclodextrin composition" means (1) a cyclodextrin derivative such that the cyclodextrin has at least one functional group on one of the cyclodextrin glucose moiety hydroxyl groups, (2) a polymer compound such that the cyclodextrin material is grafted to a functional group of the polymer or (3) with cyclodextrin directly formed into a polymer structure such that the cyclodextrin is formed into the polymer chain or polymer backbone material.

The term "produce or produce material" includes virtually any whole plant, plant part, such as a fruit, flower, cut flower, seed, bulb, cutting, root, leaf, flower, or other material that is actively respiring and, as a part of its maturation, generates ethylene as a maturation hormone.

The term "olefinic inhibitor of ethylene generation in produce" is intended to mean an olefinic compound that contains at least one olefinic double bond, has from about 3 to about 20 carbon atoms and can be aliphatic or cyclic having at least minimal ethylene antagonist or inhibition activity.

The term "modified polymer" as used in this specification means that a polymer such as a polyolefin has either a covalently bonded linking group capable to bond a cyclodextrin to a polymer or a cyclodextrin covalently bonded directly to the polymer or covalently bonded to the polymer through a linking group.

The term "polyolefin compatible" or "polymer compatible" as used herein means that a component, when added to or in contact with a composition containing modified polyolefin or modified polymer as that term is used in this specification, does not phase out of the composition and is not detrimental to the pertinent physical characteristics of the resulting polyolefin, such as tensile strength, melt index, color, odor or other physical characteristics the polyolefin or polymer would otherwise have.

The term "polymer web" as used herein means a planar structure including a coating, woven or non-woven, a flexible film, a rigid or semi-rigid film or sheet, a thermoformed packaging component or other extruded, injection molded or other such film or sheet structure that can be used in packaging technology.

DETAILED DESCRIPTION OF THE ILLUSTRATIVE EMBODIMENTS

We have found a thermoplastic composition that can be used as a non-woven fiber or woven fabric, as a film as a packaging material or in a coating there on for the packaging of produce or produce materials for the purpose of extending shelf life or slowing or stopping maturation. The thermoplastic compositions of the invention typically comprise a releasable olefinic antagonist or inhibitor of ethylene generation on produce. The inhibitor is typically introduced into the central pore of a cyclodextrin molecule. The cyclodextrin molecule is typically introduced into the polymer as a small molecule substituted cyclodextrin, a grafted substituent or into the polymer backbone or polymer chain. Such a composition typically comprises about 1.0 to 90 weight percent of a polyolefin and about 0.1 to 65 weight percent or 2 to 50 weight percent of the cyclodextrin grafted resin. The cyclodextrin moiety composition about 0.1 to 20 weight percent or 0.2 to 10 weight percent of the composition as a whole of the polymer composition. In the polymer composition, about 0.005 to 10 weight percent or 0.02 to 5 percent of the available central pores in the cyclodextrin molecule can be occupied by the olefinic inhibitor material. The overall composition of the invention can contain from about 0.01 to about 1 weight percent of the olefinic inhibitor of ethylene generation and produce or produce materials. The olefinic inhibitor itself comprises a compound having from three to about 20 carbon atoms, comprising at least one olefinic bond and comprising a cyclic, olefinic or diazodiene structure. Typically, the composition can contain about 0.001 to 1 or 0.002 to 0.5 or 0.003 to 0.2 mole of the inhibitor compound preferably 1-MCP per each mole of cyclodextrin in the composition. Specific compounds useful as the olefinic inhibitor of ethylene generation include 1-methyl cyclopropene, 1-butene, 2-butene, isobutylene, etc.

In the manufacture of the polymer compounds of the invention, we have found that careful control of water content in the polymer is important in maintaining the stability of the olefinic inhibitor of ethylene generation in the packaging product. As water is reduced, the olefinic inhibitor is more controllably maintained within the central pore structure of the cyclodextrin material until the material is used as a portion or component of produce or produce component packaging. In the manufacture of the polymer materials, the polymer containing the cyclodextrin moieties can be combined with a thermoplastic polymer material free of the cyclodextrin moieties for the purpose of manufacturing either a master batch of the polymer or the final polymer materials used in manufacturing the fiber fabric film or packaging structures of the invention. In such a composition, the polymer comprising the cyclodextrin moiety can be combined with a thermoplastic polymer. In master batch compositions, the thermoplastic polymer can contain about 1 to 65 weight percent of the thermoplastic containing the cyclodextrin moieties. In a final polymer composition used for forming packaging materials, the polymer composition contains about 0.1 to 20 weight percent of the polymer comprising the cyclodextrin moiety. In such a manufacturing step, the olefinic inhibitor of ethylene generation can be resident in the cyclodextrin molecule (e.g., as a cyclodextrin/olefinic inhibitor masterbatch to be let down into virgin thermoplastics) during the formation of produce containers, packaging or packaging components or after combining cyclodextrin with a thermoplastic material in the conversion process and subsequently loading the cyclodextrin pores with the olefinic inhibitor after the formation of produce containers, packaging or packaging components.

Preferred materials for use in the polymer compositions of the invention are polyolefins and polyolefin copolymers, including polyethylene, polypropylene, poly (ethylene-co-propylene), polyethylene-co-alpha olefin, and other similar homo- and co-polymers of alpha olefins. In one preferred mode, the polymer comprising the cyclodextrin moieties can be manufactured by grafting cyclodextrin onto a maleic anhydride modified polyolefin. Such polyolefins can contain from about 0.5 to about 20 or 0.5 to 10 weight percent maleic anhydride. Such materials can be reacted with cyclodextrin such that a hydroxyl compound of the cyclodextrin material reacts with the maleic anhydride moiety in the polyolefin backbone thus forming a polymer composition such that the maleic anhydride materials are fully reacted to form cyclodextrin modified polyolefins. Such material can contain from about 1 to about 20 weight percent cyclodextrin in the final polymer composition.

An important aspect of the invention is the method for manufacturing or introducing the olefinic inhibitor in the center pore of the cyclodextrin molecule using a process involving controlled low moisture concentration and high pressure at a moderate temperature. In manufacturing the polymer composition of the invention, the polymer comprising of cyclodextrin moiety can be exposed to the olefinic inhibitor at a molar ratio of about 0.5 to 10 moles of inhibitor per mole of cyclodextrin in an enclosed space at a pressure of about 1 to about 15 atmospheres at a temperature of about 0° C. to about 100° C. to effectively introduce the olefinic inhibitor into the central part of the cyclodextrin molecule in amounts discussed above. The moisture can be controlled such that the moisture content of the polymer is <800 ppm and the enclosed space within the treating chamber is less than about 5 ppm moisture. Alternatively the moisture content of the close space is less than about 1 percent relative humidity. In order to release the inhibitor or antagonist, the moisture contact is increased.

Lastly an important aspect of the invention is the method of controlled release of the olefinic inhibitor from packaging components or materials such that an effective concentration of the inhibitor molecule in the enclosed space within the packaging system effectively controls, inhibits or reduces maturation or ripening of the materials. In such a method, the polymer composition with the cyclodextrin compound and the olefinic inhibitor is used in manufacturing a packaging material, the produce or produce material is placed within the packaging material and in the enclosed volume within the packaging material a controlled amount of moisture or humidity is put into place within the packaging as previously descried. The moisture content at typical storage temperatures in this environment causes the release of the olefinic inhibitor from the cyclodextrin molecule. This effective concentration of the olefinic inhibitor in the void space within the packaging material maintains the produce effectively.

The cyclodextrin modified polyolefin compositions or resins can contain a blend of a polymer and a polymer containing cyclodextrin or a substituted cyclodextrin. The Polymer can comprise from about 0.1 to about 20 wt % or preferably 0.3 to 10 wt % cyclodextrin. The thermoplastic polymer compositions comprise a blend of a major proportion of a polyolefin resin and between about 1 wt % to about 65 wt % of a cyclodextrin modified polyolefin resin based on the polymer composition; and from about 0.0001 wt % to about 3 wt %, or about 0.0002 to 2 wt %, or about 0.0005 wt % to about 1 wt % of a volatile olefinic inhibitor or antagonist compound.

Inhibitor Compound

The inhibitor compound of the invention includes a $C_{4-20}$ olefin compound, preferably with the double bond adjacent to a terminal carbon atom. Cyclopropene derivatives can act as an inhibitor, such as the following formula I. In formula I, $R^1$ is independently hydrogen or a $C_{1-16}$ alkyl, $R^2$ is independently hydrogen or a $C_{1-16}$ alkyl and $R^3$ and $R^4$ are independently hydrogen or a $C_{1-16}$ alkyl with a proviso that at least one of $R^1$ or $R^2$ is methyl.

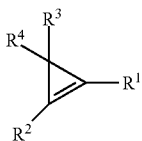

Cyclodextrin

Cyclodextrin (CD) is a cyclic oligomer of α-D-glucopyranoside units formed by the action of certain enzymes such as cyclodextrin glycotransferase (CGTase). Three cyclodextrins (alpha, beta, and gamma) are commercially available consisting of six, seven and eight α-1,4-linked glucose monomers, respectively. The most stable three-dimensional molecular configuration for these oligosaccharides is a toroid with the smaller and larger opening of the toroid presenting primary and secondary hydroxyl groups. The specific coupling of the glucose monomers gives the CD a rigid, truncated conical molecular structure with a hollow interior of a specific volume. This internal cavity, which is lipophilic (i.e., is attractive to hydrocarbon materials when compared to the exterior), is a key structural feature of the cyclodextrin, providing the ability to complex molecules (e.g., aromatics, alcohols, halides and hydrogen halides, carboxylic acids and their esters, etc.). The complexed molecule must satisfy the size criterion of fitting at least partially into the cyclodextrin internal cavity, resulting in an inclusion complex.

| CYCLODEXTRIN TYPICAL PROPERTIES | | | |
|---|---|---|---|
| CD PROPERTIES | α-CD | β-CD | γ-CD |
| Degree of polymerization (n=) | 6 | 7 | 8 |
| Molecular Size (A°) | | | |
| inside diameter | 5.7 | 7.8 | 9.5 |
| outside diameter | 13.7 | 15.3 | 16.9 |
| height | 7.0 | 7.0 | 7.0 |
| Specific Rotation $[\alpha]^{25}_D$ | +150.5 | +162.5 | +177.4 |
| Color of iodine complex | Blue | Yellow | Yellowish Brown |
| Solubility in Distilled water (g/100 mL) 25° C. | 14.50 | 1.85 | 23.20 |

The oligosaccharide ring forms a torus, as a truncated cone, with primary hydroxyl groups of each glucose residue lying on a narrow end of the torus. The secondary glucopyranose hydroxyl groups are located on the wide end. The parent cyclodextrin molecule, and useful derivatives, can be represented by the following formula (the ring carbons show conventional numbering) in which the vacant bonds represent the balance of the cyclic molecule:

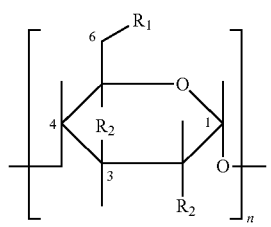

The CD's internal cavity size (i.e., α, β, γ) can be considered and the functional group modification can be suitable for changing the desired bulk polymer and surface polymer characteristics in addition to forming an inclusion complex with targeted volatiles or impurities. To achieve a specific result, more than one cavity size and functional group may be necessary.

According to the present disclosure, the cyclodextrin material is a compound containing as an inclusion complex of the inhibitor or antagonist compound, formed within the central pore of each cyclodextrin moiety in the polymer composition of the invention. The olefinic antagonist or inhibitor compound can comprise a $C_{4-20}$ compound having at least one olefinic group. As a result of the inclusion of the olefinic inhibitor compound in the central pore of the cyclodextrin molecule, any polymer composition containing a cyclodextrin moiety can contain a large fraction of the cyclodextrin moiety with the olefinic inhibitor as an inclusion complex within the central pore of the cyclodextrin ring. In certain inventions, the central pore is used as a binding location for permeant but in this invention, the central pore is used as a storage location for the olefinic inhibitor or antagonist which can be controllably released from the polymer composition to control maturation in produce or produce materials.

Cyclodextrin Derivatives

The thermoplastic composition of the invention can contain a cyclodextrin derivative. The cyclodextrin derivative is compatible with the polymer material. The cyclodextrin derivative can be combined with the olefinic inhibitor such that the olefinic inhibitor is formed as an inclusion complex within the central pore. Such polymer materials containing the substituted cyclodextrin can be used in a method of controlled release of the olefinic inhibitor from the composition in control or reduction of ripening of the produce or produce materials. The methods of manufacturing the polymer with a cyclodextrin having the olefinic inhibitor are substantially similar to the polymer compositions containing the cyclodextrin moiety. Further, the polymer compositions containing the substituted cyclodextrin material with the olefinic inhibitor can be used in methods of controlled release of the olefinic inhibitor using substantially similar process steps.

CD molecules have available for reaction with a functionalized polyolefin the primary hydroxyl at the six position of the glucose moiety, and at the secondary hydroxyl in the two and three positions. Because of the geometry of the CD molecule, and the chemistry of the ring substituents, all hydroxyl groups are not equal in reactivity. However, with care and effective reaction conditions, dry CD molecules can be reacted to obtain substituted CD. CD with selected substituents (i.e. substituted only on the primary hydroxyl or selectively substituted only at one or both the secondary hydroxyl groups) can also be grafted if desired. Directed synthesis of a derivatized molecule with two different substituents or three different substituents is also possible. These substituents can be placed at random or directed to a specific hydroxyl. Further, CD alcohol derivatives (e.g., hydroxyethyl and hydroxypropyl) and amino derivatives can be reacted to make a grafted CD.

The preferred preparatory scheme for producing a substituted CD material having compatibility with polyvinyl resin involves reactions at the primary or secondary hydroxyls of the CD molecule. It is meant that a hydroxyl functionality of the CD reacts with the reactive component of the substituent forming compound to form a substituted cyclodextrin reaction product. The formation of a bond on either the primary or secondary ring hydroxyls of the CD molecule involves well-known reactions. The primary —OH groups of the cyclodextrin molecules are more readily reacted than the secondary groups. However, the molecule can be substituted on virtually any position to form useful compositions. Broadly, we have found that a wide range of pendant substituent moieties can be used on the molecule. These derivatized cyclodextrin molecules can include alkylated cyclodextrin, hydrocarbyl-amino cyclodextrin, and others. The substituent moiety should include a region that provides compatibility to the derivatized material.

Amino and azido derivatives of cyclodextrin having pendent thermoplastic polymer containing moieties can be used in the sheet, film or container of the invention. The sulfonyl derivatized cyclodextrin molecule can be used to generate the amino derivative from the sulfonyl group substituted cyclodextrin molecule via nucleophilic displacement of the sulfonate group by an azide ($N_3^{-1}$) ion. The azido derivatives are subsequently converted into substituted amino compounds by reduction. Such derivatives can be manufactured in symmetrical substituted amine groups (those derivatives with two or more amino or azido groups symmetrically disposed on the cyclodextrin molecule or as a symmetrically substituted amine or azide derivatized cyclodextrin molecule). Due to the nucleophilic displacement reaction that produces the nitrogen containing groups, the primary hydroxyl group at the 6-carbon atom is the most likely site for introduction of a nitrogen-containing group. Examples of nitrogen containing groups that can be useful in the invention include acetylamino groups (—NHAc), alkylamino including methylamino, ethylamino, butylamino, isobutylamino, isopropylamino, hexylamino, and other alkylamino substituents. The amino or alkylamino substituents can further be reactive with other compounds that react with the nitrogen atom to further derivatize the amine group. Other possible nitrogen containing substituents include dialkylamino such as dimethylamino, diethylamino, piperidino and piperizino.

The cyclodextrin molecule can be substituted with heterocyclic nuclei including pendent imidazole groups, histidine, imidazole groups, pyridino and substituted pyridino groups.

Cyclodextrin Modified Polyvinyl Polymers

The cyclodextrin can also be used as a part of a thermoplastic polymer. The cyclodextrin can be a pedant group or formed in the polymer backbone. Cyclodextrin-modified polymers including final polymers such as a polyolefin resin can be prepared by covalently grafting a cyclodextrin moiety onto a polyolefin or polyolefin blend. The grafting can be achieved by reacting a functional group, such as a hydroxyl group of cyclodextrin (CD) with a functional group, such as an epoxy acid, acid chloride or anhydride moiety, on the polymer or blend to form a bond between the cyclodextrin and the polyolefin. In another embodiment, an anhydride or epoxide component of the functionalized polymer can be used to form a reaction product. For example, a primary hydroxyl on the cyclodextrin reacts with an epoxy, acid chloride or a maleic anhydride moiety of the resin under conditions that convert substantially all anhydride groups to a half-ester.

The modified polymers and the cyclodextrin grafted polymer compositions, according to the present disclosure, are useful in fibers, woven or non-woven fabrics, extruded or molded structures such as thin films, laminates, semi-rigid films and rigid containers. For instance, these structures provide functional properties for a flexible packaging structure, insert, closure or other packaging component. Polymers that can contain a cyclodextrin moiety in the backbone of the polymer can take a number of forms. The polymer can be a linear polymer having repeating units derived from the cyclodextrin structure. The polymer can have alternating residues derived from cyclodextrin and one or more other monomers, typically in a polycondensation format. Further, the polymer can take the form of a later polymer or a polymer formed by extensively crosslinking the cyclodextrin molecule into a highly crosslinked structure. Cyclodextrin can be crosslinked with 1-chloro-2,3epoxypropene to form a highly crosslinked cyclodextrin structure. A linear tube of cyclodextrins can be made by condensing the cyclodextrin in a linear tube wherein in the polymer structure, the cyclodextrin is formed as the rise of a "ladder" in a structural format. Linear and highly branched cyclodextrin polymers can be made by polycondensation of cyclodextrins with an epoxy compound such as ethylcholorohydrin to form a cyclodextrin ethylcholorohydrin copolymer. Linear compositions can be made by reacting cyclodextrin molecules with amino ethyls and then condensing with polycondensation reactants as shown in Hwang et al., "Effects of Structure of β-Cyclodextrin-Containing Polymers on Gene Delivery," *Bioconjugate Chem.*, 2001, 12(2), pp. 280-290.

Embodiments in accordance with the present disclosure also include a chip with a major dimension of less than about 10 mm and a weight of about 20 to 50 mg, whereby the chip comprises compositions of the present disclosure as described above. Further embodiments include a container comprising an enclosed volume surrounded by a polyolefin web, the web comprised of compositions as described above, such containers being useful, for example, in the packaging of food. Additionally, fibers and films prepared from the compositions of the present disclosure are also included in accordance with the present disclosure.

The addition of maleic anhydride to a normal alpha olefin generates an alkenyl succinic anhydride. The "ene" reaction is an indirect substituting addition. It involves the reaction of an olefin with an allylic hydrogen (ene) with an enophile, e.g., maleic anhydride. The reaction results in a new bond forming between two unsaturated carbons and the allylic hydrogen transfers to the maleic anhydride through a cyclic transition state. The reaction can be carried out using a range of normal alpha olefins from 1-butene to $C_{30+}$ normal alpha olefin wax. The maleic anhydride molecule supplies the reactive anhydride functionality to the alkenyl succinic anhydride, while the long chain alkyl portion provides the hydrophobic properties.

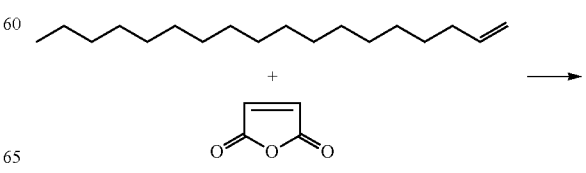

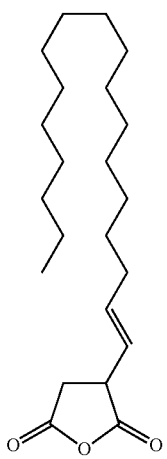

Alkenyl succinic anhydride materials are available commercially such as maleic anhydride derivatives comprise products with an alkenyl backbone that starts at $C_8$ and progresses through to $C_{18}$. By changing the nature of the starting alkene (i.e. straight chain vs. isomerize form) the physic-chemical properties of the resultant alkenyl succinic anhydride (e.g. solid vs. liquid form at room temperature) can be modified. Commercially available useful materials include: dodecenylsuccinic anhydride, n-tetradecenyl succinic anhydride, hexadecenyl succinic anhydride, iso-hexadecenyl succinic anhydride, octadecenyl succinic anhydride, and tetrapropenyl succinic anhydride. The polymethylene chains are shown in a specific conformation for convenience purposes and do not conform to these structures in the composition of the invention.

Hydrocarbyl-substituted succinic acids and anhydrides are preferred high-molecular weight carboxylic acids and anhydrides. These acids and anhydrides can be prepared by reacting maleic anhydride with an olefin or a chlorinated hydrocarbon such as a chlorinated polyolefin. The reaction involves merely heating the two reactants at a temperature in the range of about 100° C. to about 300° C., or about 100° C. to 200° C.

The product from this reaction is a hydrocarbyl-substituted succinic anhydride wherein the substituent is derived from the olefin or chlorinated hydrocarbon. The product may be hydrogenated to remove all or a portion of any ethylenically unsaturated covalent linkages by standard hydrogenation procedures, if desired. The hydrocarbyl-substituted succinic anhydrides may be hydrolyzed by treatment with water or steam to the corresponding acid. The high-molecular weight hydrocarbyl-substituted succinic acids and anhydrides can be represented by the formula:

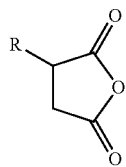

Wherein R is the hydrocarbyl substituent. Preferably R contains from about 10 to about 500 carbon atoms, or from about 15 to about 500 carbon atoms, or from about 18 to about 500 carbon atoms.

Thermoplastic Resins

Polyolefins such as polyethylene and polypropylene can be use in the invention as well as copolymers of ethylene propylene and other alpha olefin monomers.

Commercial polyolefin functionalization is achieved using solution, melt and solid state routes known in the art. The process covalently bonds monomers onto vinyl polymers or onto polyolefin polymers including copolymers of olefins with other monomers, such as vinyl monomers. Polyolefins useful in modified or un-modified embodiments according to the disclosure include poly(ethylene) or PE, poly(propylene) or PP, poly(ethylene-co-propylene) or PEP, ethylene/methyl acrylate copolymer, and ethylene/ethyl acrylate copolymer. The polyolefins can be functionally modified with unsaturated compounds such as unsaturated anhydrides and carboxylic acids. Any packaging grade of a vinyl polymer can be used.

Polyolefin and functionalized polyolefins have extensive industrial applications such as coextrusion tie resins in multi-layer films and bottles for the food industry, compatibilizers for engineering polymers and plastic fuel tank tie resins for the automotive industry, flexibilization and compatibilization of halogen free polymers for cables and for filler materials used in roofing construction. Functionalized polyolefins can also find application in containers for food contact. Functionalized polyolefins useful in the present disclosure are maleated polyethylene and polypropylene (OREVAC™ and LOTRYL™ available from Arkema, Philadelphia, Pa., PLEXAR® resins available from EQUISTAR, Rotterdam, The Netherlands, ADMER® resin from Mitsui Chemicals, Tokyo, Japan, FUSABOND® resins from DuPont, Wilmington, Del., OPTIM™ resins from MANAS, India and EXXELOR™ from Exxon/Mobil, Houston, Tex.), functionalized EP, EVA and EPDM (such as ethylene-propylene-butadiene or, ethylene-propylene-1,4-hexadiene polymers) ethylene-octene copolymers, ethylene-n butyl acrylate-maleic anhydride, ethylene-ethylacrylate-maleic anhydride terpolymers and copolymers of ethylene-glycidyl methacrylate and the like. The ethylene-propylene-1,4-hexadiene copolymer can be represented as:

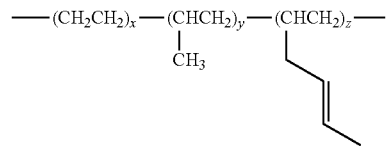

wherein x is selected to obtain about 70 to 90 wt % ethylene, y is selected to obtain about 10 to 30 wt % propylene and z is selected to obtain up to about 5 wt % 1,4-hexadiene. The vacant bonds are linked to similar groups, H, or end groups.

Other polyolefins which are known in the art can be used in compositions of the present invention to impart desirable processing or end product characteristics. For example, polybutene can be added to increase fiber strength. Other olefins that can be added to produce copolymers or blends include alpha olefins such as 1-hexene and 1-octene to impart flexibility.

Compositions in accordance with the present disclosure can be prepared using reactive extrusion by feeding a dry cyclodextrin, or derivative thereof, (<0.10% moisture), a functionalized polyolefin and optionally a second polyolefin, into an extruder at temperatures such that the cyclodextrin reacts with the functionalized polyolefin as the molten polymer and cyclodextrin are transported through the extruder to form a reaction product containing, for example, an ester group which covalently bonds the cyclodextrin to the polyolefin. The ratio of functionalized polyolefin to non-functionalized polyolefin can be adjusted for a specific application and conversion process.

The present invention is directed to a stoichiometric reaction product of a cyclodextrin (CD) and a graft linking agent (i.e., anhydride, epoxide, etc.), and a non-volatile and polymer compatible carboxylic acid, resulting in a modified polymer especially suited as a masterbatch which can be subsequently let down with one or more non-functionalized thermoplastic polymers and thermoplastic elastomers at a weight ratio of one (1) parts of the masterbatch composition to ten (10) to twenty (20) parts of non-functionalized polymer. A maleic acid, fumaric acid or maleic anhydride functionalized material is useful for bonding CD to the polyolefin. The stoichiometric ratio for melt grafting is calculated on a gram-mole (gram-formula-weight) basis where one (1) gram-mole of CD ($\alpha$, $\beta$ or $\gamma$ form) is equivalent to one (1) gram-mole the grafted anhydride, glycidyl and carboxylic acid moiety.

The structures of the invention can be made by coating a liquid containing the cyclodextrin compound and the complexed 1-MCP onto a substrate. The substrate to be coated can be in any form, such as a flexible film, web, nonwoven or woven material or foam. Any of the substrates mentioned above can be used but preferred substrates are films and fiber in the form of woven or non-woven fabric. The substrate can be porous or nonporous and can be made of materials such as plastic, paper or fabric from either natural or synthetic fiber.

The coating composition can contain the grafted cyclodextrin or the substituted cyclodextrin in a coatable solution, dispersion or suspension. The coating can be made by combining coating materials in a liquid phase. Such liquids can contain aqueous materials or non-aqueous liquids or as an aqueous phase containing non-complexing, water-soluble co-solvents (e.g., glycol ethers). Aqueous coatings are preferred due to low costs and ease of manufacture. As discussed elsewhere the moisture content of the final coating is important for control of the 1-MCP release characteristics. Solvent coating can be made and have the advantage of not containing substantial quantities of water that require a drying step. Many solvents require shorter and cooler drying cycles.

The coating can be made by dispersing or dissolving the coating constituents in the liquid phase and mixing until uniform. Such coating compositions contain a major portion of the liquid phase typically about 50 to 70 wt. % of liquid. The coating can contain about 0.5 to 20 wt % of the cyclodextrin, calculated as cyclodextrin in the form of the substituted cyclodextrin or the polymer grafted cyclodextrin. Depending on the amount of cyclodextrin in the cyclodextrin compound, the coating composition can contain about 5 to 40 wt. % of the cyclodextrin compound. The cyclodextrin is typically introduced into the coating composition in the form of small particulate or small particle dispersion. Such small particles can be formed prior to addition to the liquid phase but can also be formed mechanically after addition.

Such coating compositions typically comprise vinyl polymers adapted for coating purposes. Such polymers are typically formulated into aqueous solutions that can also contain rapid drying solvent materials. Typical coating compositions comprise homopolymers, copolymers, terpolymers, etc. including acetate, acrylic, sytrenic, polysaccharides, acrylamide/acrylate copolymers, and carboxymethylcellulose and other polymer systems; adjuvants or excipients, such as a gelling agent, including naturally occurring compounds such as carrageenan and gelatin, extenders, binders, lubricants, surfactants and/or dispersants, wetting agents, spreading agents, dispersing agents, stickers, adhesives, defoamers, thickeners, emulsifying agents, inorganic agents such as calcium chloride, magnesium chloride, lithium chloride, zinc chloride, magnesium nitrate, and aluminum nitrate; and combinations and mixtures thereof.

A typical aqueous coating formulation can contain the following:

| | |
|---|---|
| Water | 40-80% |
| Binder (EVA or SBA) | 20-40% |
| Pigment | 0-40% |

Surfactants, Leveling Agents, Defoamers, Stabilizers
A typical solvent based coating formulation can contain the following:

| | |
|---|---|
| Solvent | 40-80% |
| Co-Solvent | 0-5% |
| Binder (numerous polymers) | 20-40% |
| Pigment | 0-40% |

Leveling Agents Stabilizers

The term "produce" material is used in a generic sense herein, and includes live respiring and ethylene generating plant materials. Included are woody-stemmed plants such as trees and shrubs. Plants to be treated by the methods described herein include whole plants and any portions thereof, such as field crops, potted plants, cut flowers (stems and flowers), and harvested fruits and vegetables. These include any plant that matures or ripens due to the presence of or the generation of ethylene as a maturation hormone. The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the prolongation of the life of ornamentals such as potted plants, cut flowers, shrubbery, and dormant seedlings, in some plants (e.g., pea) the inhibition of growth, and in other plants (e.g., rice) the stimulation of growth. Additional ethylene responses or ethylene-type responses that may be inhibited by active compounds of the present invention include, but are not limited to, auxin activity, inhibition of terminal growth, control of apical dominance, increase in branching, increase in tillering, changing biochemical compositions of plants (such as increasing leaf area relative to stem area), abortion or inhibition of flowering and seed development, lodging effects, stimulation of seed germination and breaking of dormancy, and hormone or epinasty effects.

Vegetables can be treated by the method of the present invention to inhibit ripening and/or senescence including leafy green vegetables such as lettuce, spinach and cabbage. Various roots are included such as potatoes and carrots. Plants from bulbs, such as tulips, shallots, onions; herbs, such as basil, oregano, dill; as well as soybean, lima bean, pea, corn, broccoli, cauliflower, and asparagus. Fruits include tomatoes, apples, bananas, pears, papaya, mangoes, peaches, apricots, nectarines; citrus including orange, lemon, lime, grapefruit, tangerines; other fruits such as kiwi; melons such as cantaloupe, musk melon, pineapple, persimmon; various small fruits including berries such as strawberries, blueberries and raspberries; green beans, cucumber and avocado. Ornamental plants that have ornamental character from flower, leaf, stem (bamboo) such as potted or cut flowers can be helped with the invention. Azalea, hydrangea, hibiscus, snapdragons, poinsettia, cactus, begonias, roses, tulips, daffodils, petunias, carnation, lily, gladiolus, alstroemeria, anemone, columbine, aralia, aster, bougainvillea, camellia, bellflower, cockscomb, chrysanthemum, clematis, cyclamen, freesia, and orchids are included. Plants that can be treated by the method of the present invention include cotton, apples, pears, cherries, pecans, grapes, olives, coffee, snapbeans and fig, as well as dormant seedlings such as various fruit trees including apple, ornamental plants, shrubbery, and tree seedlings. In addition, shrubbery can be treated by the method of the present invention including privet, photinea, holly, ferns, scheffiera, aglaonema, cotoneaster, barberry, waxmyrtle, abelia, acacia and bromeliades. Also included are living or respiring plants and plant material without edible or ornamental materials including shoots, planting stock, grafting stock, seeds, bulbs, planting eyes, flowers, etc.

The following exemplary section contains examples of thermoplastic materials in the form of film and fiber and also contains data showing the properties of the thermoplastic material with respect to the use of the alternate inhibitor compound. In these data the compound 1-butene is used as a model compound. This compound is used since it is an inexpensive material that can mimic the properties of 1-MCP in both introducing the inhibitor material into the thermoplastic materials of the invention and can mimic the release properties of the material under use conditions.

In the polymer materials of the invention the components can be used at the following levels depending on the formation of either a masterbatch or the final blended polymer material, the nature of the web and the produce contained.

Polymer Compositions

Based on the Masterbatch Material or the Final Blended Material

| Component | Wt. % | Wt. % | Wt. % |
|---|---|---|---|
| Inhibitor | 0.0001 to 3 | 0.02 to 2 | 0.01 to 1 |
| Cyclodextrin | 0.2 to 20 | 0.3 to 10 | 0.5 to 7 |
| CD-Grafted polymer | 1 to 65 | 2 to 50 | 5 to 45 |
| Polymer | 1 to 90 | 1 to 80 | 5 to 70 |

Examples and Data

Fiber Example 1:
Spunbond Fiber produced on a 1 meter Reifenhauser spunbonded fabric line having a basis weight of 21.4 gm/sq meter and 20 g fibers and having:
1.5% α-cyclodextrin grafted onto the polyolefin blend (Cavamax W6A lot 60F203 manufactured by Wacker Chemie)
5.0% Fusabond 411D lot VR30087227 manufactured by DuPont
5.0% Fusabond 353D lot VR30091736 manufactured by DuPont
2.8% Poly B 0300M manufactured by Basell
86% polyolefin resin (Polypropylene 3155 manufactured by ExxonMobil)
Control fiber example 1: SB Spunbond Fiber produced on a 1 meter Reifenhauser spunbond line having a basis weight of 21.4 gm-m², 20μ fibers.
100% polypropylene 3155 (ExxonMobil)
Film Example 2:
Three layer coextruded blown polyethylene film structure—6 mil thickness.
  Outside sealant layers (2 mil each):
    2% α-cyclodextrin grafted onto the polyolefin (Cavamax W6A lot 60F203 manufactured by Wacker Chemie).
    21.5% Integrate NE542-013 manufactured by Equistar.
    38.2% Affinity PF1140G manufactured by Dow Plastics.
    38.3% Exact 8852G manufactured by ExxonMobil.
  Core (2 mil): Mobil LGA 105 low density polyethylene.

Film Example 2:
Three layer coextruded blown polyethylene film structure—6 mil thickness.
  Outside sealant layers (2 mil each):
    2% α-cyclodextrin grafted onto the polyolefin blend (Cavamax W6A lot 60F203 manufactured by Wacker Chemie).
    50% Affinity PF1140G manufactured by Dow Plastics.
    50% Exact 8852G manufactured by ExxonMobil.
  Core (2 mil): Mobil LGA 105 low density polyethylene
Coating Example 1:

| | |
|---|---|
| Deionized Water | 85.75% |
| Airflex ®920 Emulsion (Air Products and Chemicals, Inc; Allentown, PA18195) | 9.50% |
| Pluronic 31R1 manufactured by BASF. | 0.75% |
| α-cyclodextrin (Cavamax W6F manufactured by Wacker Chemie) | 4.00% |

Film and Spunbond Fiber Sample Production Procedure

First sample set: Each of Film example 2 samples and control film example 2 samples were cut into 4"×4" sheets.
Second sample set: Spun-bond fiber example 1 samples and control fiber example 1 samples were cut into 8.3"×8.3" sheets.

The first set of film was found to have a moisture content of 0.13%. The film was previously stored in a storage room at 20° C. and 50% humidity for greater than 6 weeks.

The first set of fiber was found to have a moisture content of 0.17%. The fiber was stored in uncontrolled temperature and humidity warehouse space for greater than 6 weeks.

The second set of samples was placed in a vacuum oven to dry. The vacuum was held at greater than 0.1 mm-Hg for a period of 24 hours at a temperature of 100° C. for the fiber and 60° C. for the films. The dried samples of film and fiber had a moisture content of <0.08%.

For both the first sample set and second sample set, 75 of the each of the four kinds of sheets were placed in separate 3 liter Tedlar gas sample bags. The Tedlar bags, which were cut open to insert the sheets, were then resealed using a direct heat sealer after the sheets were in place. Once sealed all remaining air trapped in the Tedlar bags was withdrawn with a glass syringe via the stainless steel fittings incorporated into the bags. The evacuated bags were then injected with 150 mL of 99.0% 1-butene gas. The 1-butene was used as a surrogate for 1-MCP since both compounds have ethylene generating inhibitory capacity, have similar molecular size, four carbon atoms and one olefinic bond.

In the case of the bag with the Film example 2 samples, this amount of the gas translates to a 1-butene to α-CD molar ratio of 4.5:1. In the case of the bag with the fiber example 1 samples, this amount of the gas translates to a 1-butene to α-CD molar ratio of 5.9:1. Oversaturation of 1-butene is desired to encourage complexation. The Tedlar bags and their contents were then placed in a 5 L pressure vessel. The pressure vessel was pressurized by the introduction of nitrogen to 120±5 psig at 20° C. The vessel was held at this pressure and temperature for a period of 24 hours. After 24 hours of pressurization, the Tedlar bags were removed from the vessel; the sheets were removed from the bags and exposed to ambient conditions (20° C. and 50% RH) for amounts of time ranging from one hour to one week.

Sample Production Procedure for Coated Meltblown Fiber

Samples of meltblown (MB) fiber which contained no CD were cut into 6"×6" sheets. These sheets were coated with either a CD containing coating or a control coating that had zero CD content. Both coatings were 85.76% water, 9.52% Airflex® 920 Emulsion, and 0.75% Pluronic surfactant. The Airflex® 920 Emulsion is 55% solids and contains vinyl acetate polymers, water and 7732-18-5 biocide. The Pluronic is specifically made up of the tri-block copolymer poly(propylene glycol)-block-poly(ethylene glycol)-block-poly(propylene glycol) and has an HLB (hydrophile-lipophile balance) of 1. The CD containing coating had a 4.00% alpha cyclodextrin content. The control coating had a 4.00% D-(+)-maltose monohydrate content.

The coatings were applied to the fiber until the fiber sample was completely wetted out. Immediately after the coating was applied, the samples were hung to dry in ambient conditions. The fiber samples were inverted periodically so that the coating dried evenly across the surface of the fiber. Once dry to the touch, the fiber samples were placed in the vacuum oven to dry. The vacuum was held at <0.1 mmHg for a period of 24 hours at a temperature of 100° C. The dried samples of fiber had a moisture content of <0.18%.

50 of the control and CD coated meltblown fiber sheets were then placed in two separate Tedlar bags. The Tedlar bags, which were cut open to insert the sheets, were then resealed using a direct heat sealer after the sheets were in place. Once sealed, all of the remaining air trapped in the Tedlar bags was withdrawn with a glass syringe via the stainless steel fittings that are attached to the bags. The evacuated bags were then injected with 100 mL of 99.0% 1-butene gas. This amount of the gas translates to a 1-butene to α-CD molar ratio of 4.5:1. The Tedlar bags and their contents were then placed in a 5 L pressure vessel. The pressure vessel was pressurized with nitrogen to 120±5 psig. The vessel was held at this pressure for a period of 24 hours. After pressurization, the Tedlar bags were removed from the vessel; the sheets were removed from the bags and exposed to ambient atmosphere conditions (20° C. and 50% RH) for 24 and 48 hours prior to analysis.

Analytical Test Method

The static adsorption test method is most easily explained in terms of a test substrate (a sheet of film or fiber) surrounded by a fixed volume (e.g., a volume held within sealed glass bottle). Test substrate and volume were initially free of the test solute (1-butene inhibitor) inside the close-volume bottle. At time zero, a specific weight of the test substrate was placed inside the sealed glass bottle (250 mL serum bottle with Teflon faced silicone screw cap seal). Headspace concentrations of 1-butene were measured at different time intervals following introduction of test substrate into bottle. The 1-butene headspace concentration surrounding the test structure was quantified using gas chromatography.

A gas chromatograph (HP 5890) operated with flame ionization detection (FID), a six-port heated sampling valve with 1 mL sampling loop and data collection software (HP ChemStation A06.03-509) was used to measure the 1-butene headspace concentration. Static headspace concentration was determined in test samples using a five point 1-butene calibration curve measured in μL of 1-butene per 250 mL bottle volume and presented as μL/L or parts per million (vol./vol.).

Test substrates were placed into a 250 mL serum bottle with Teflon® faced silicone septa. The serum bottle was maintained at room temperature (20° C.) during the test interval. At each sampling interval, the serum bottle headspace was sampled by removing 1 mL of gas from the sample bottle using a Valco Instrument six port manual gas sampling valve (Valco #DC6WE) interface directly to the GC column.

HP 5890 GC
Zone Temperatures:

|  | Setpoint |
| --- | --- |
| Six port valve | 120° C. |
| Detector (FID) | 150° C. |
| Over Zone: |  |
| Equib Time | 0.00 min. |

Oven Program:

|  | Setpoint |
| --- | --- |
| Isothermal Temp.: | 150° C. |
| Initial Time: | 1.20 min. |
| Runtime (min): | 1.20 min. |

The 1-butene working standard was prepared by diluting 10 mL of 99.0% pure 1-butene gas (Scotty Gas #BUTENE01) in a Tedlar® gas sampling bag containing 1 liter of air. The 1-butene working standard concentration was 10,226 μL/L (PPM).

Calibration standards were prepared at five concentration levels by injecting via a 250 μL gas tight syringe (Hamilton Gastight® #1725) 50, 100, 200, 300 and 400 μL of the working standard into 250 mL the serum bottles fitted with Teflon® faced silicone septa. ChemStation software was used to calculate a 1-butene response factor using a linear regression equation. The 1-butene standard curve correlation coefficient was 0.999.

The test substrate was placed into a 250 mL serum bottle and left alone for one hour at room temperature conditions (20° C.). After this one hour period the headspace was analyzed to obtain a precise 1-butene headspace concentration. The headspace was analyzed by GC/FID. Parenthetically, little or no desorption from the test substrate took place in the first hour because of the lack of humidity in the headspace of the jar.

After the initial headspace sample was taken, 50 μL of deionized water was injected into the jar to create a 100% humid atmosphere inside the jar. Care was taken so that the liquid water did not come in direct contact with the film or fiber sample. The water vapor in the volume equilibrated throughout the volume. One hour after injection of the water a second headspace sample was analyzed. A final headspace sample was analyzed 24 hours after the injection of water. Samples are analyzed in quadruplicate and values averaged. Desorption is determined by the difference from the initially measured 1-butene concentration at 1 hour and the later headspace sampling times.

1-Butene Desorption Data with and without Humidification for Spunbond (SB) Fiber Samples as a Function of Atmospheric Exposure

TABLE 1

| Atmospheric Exposure Time (hr) | SB Control Dry (ppm 1-butene) | SB Control Humidified 1 hr (ppm 1-butene) | SB Control Humidified 24 hr (ppm 1-butene) | SB Fiber Example 1 Dry (ppm 1-butene) | SB Fiber Example 1 Humidified 1 hr (ppm 1-butene) | SB Fiber Example 1 Humidified 24 hr (ppm 1-butene) |
| --- | --- | --- | --- | --- | --- | --- |
| 1 | 3.36 | 4.07 | 5.63 | 24.32 | 32.12 | 37.71 |
| 4 | 0.70 | 0.77 | 1.92 | 1.89 | 5.96 | 10.24 |

TABLE 1-continued

| Atmospheric Exposure Time (hr) | SB Control Dry (ppm 1-butene) | SB Control Humidified 1 hr (ppm 1-butene) | SB Control Humidified 24 hr (ppm 1-butene) | SB Fiber Example 1 Dry (ppm 1-butene) | SB Fiber Example 1 Humidified 1 hr (ppm 1-butene) | SB Fiber Example 1 Humidified 24 hr (ppm 1-butene) |
|---|---|---|---|---|---|---|
| 6 | 0.24 | 0.39 | 1.42 | 0.78 | 4.00 | 8.05 |
| 24 | 0.32 | 0.33 | 0.74 | 0.74 | 3.02 | 5.93 |
| 48 | 0.00 | 0.19 | 0.49 | 0.19 | 2.09 | 3.39 |
| 72 | 0.00 | 0.10 | 0.70 | 0.16 | 1.77 | 2.98 |
| 144 | 0.00 | 0.20 | 0.16 | 0.00 | 1.41 | 1.86 |

Note:
SB fiber dried immediately prior to 1-Butene pressurization.

These data show the average amount of 1-butene in the headspace of 250 mL jars containing sheets of SB fiber that are dry, humidified 1 hour, and humidified 24 hours. The fiber sheets have been exposed to the atmosphere (20° C. and 50% RH) for varying lengths of time after pressurized exposure to 1-butene. Moisture content of samples was <0.08% prior to 1-butene pressurization. In the humidified samples of the invention the release of the 1-butene model compound was achieved through 144 hours or 6 days. In sharp contrast to the control samples containing no inhibitor and the dry samples, both failed to maintain an effective release in comparison to the examples of the invention.

1-Butene Desorption Data with and without Humidification for Film Samples as a Function of Atmospheric Exposure

TABLE 2

| Atmospheric Exposure Time (hr) | Control Film Dry (ppm 1-butene) | Control Film Humidified 1 hr (ppm 1-butene) | Control Film Humidified 24 hr (ppm 1-butene) | Film Example 2 Dry (ppm 1-butene) | Film Example 2 Humidified 1 hr (ppm 1-butene) | Film Example 2 Humidified 24 hr (ppm 1-butene) |
|---|---|---|---|---|---|---|
| 1 | 2.43 | 2.42 | 2.53 | 19.48 | 28.72 | 29.62 |
| 4 | 0.27 | 0.19 | 0.35 | 1.14 | 8.99 | 10.14 |
| 6 | 0.00 | 0.15 | 0.25 | 0.59 | 7.44 | 9.07 |
| 24 | 0.00 | 0.11 | 0.14 | 0.59 | 5.28 | 6.35 |
| 48 | 0.00 | 0.07 | 0.16 | 0.08 | 3.69 | 4.59 |
| 72 | 0.00 | 0.03 | 0.16 | 0.15 | 3.11 | 3.63 |
| 144 | 0.00 | 0.00 | 0.00 | 0.00 | 2.13 | 2.19 |

Note:
Film vacuum dried immediately prior to 1-Butene pressurization.

These data show the average amount of 1-butene in the headspace of 250 mL jars containing sheets of film that are dry, humidified 1 hour, and humidified 24 hours. The film sheets have been exposed to the atmosphere (20° C. and 50% RH) for varying lengths of time after pressurized exposure to 1-butene. Moisture content of samples was <0.08% prior to 1-butene pressurization. In the humidified samples of the invention the release of the 1-butene model compound was achieved through 144 hours or 6 days. In sharp contrast to the control samples containing no inhibitor and the dry samples, both failed to maintain an effective release in comparison to the examples of the invention.

1 Butene Desorption Data with and without Humidification for Spunbond (SB) Fiber Stored in Uncontrolled Atmosphere for Six Weeks as a Function of Atmospheric Exposure

TABLE 3

| Atmospheric Exposure Time (hr) | Control SB Dry (ppm 1-butene) | Control SB Humidified 1 hr (ppm 1-butene) | Control SB Humidified 24 hr (ppm 1-butene) | SB Fiber Example 1 Dry (ppm 1-butene) | SB Fiber Example 1 Humidified 1 hr (ppm 1-butene) | SB Fiber Example 1 Humidified 24 hr (ppm 1-butene) |
|---|---|---|---|---|---|---|
| 4 | 3.68 | 4.98 | 8.90 | 5.70 | 8.21 | 13.99 |
| 24 | 0.25 | 0.31 | 0.39 | 0.28 | 0.32 | 0.11 |
| 48 | 0.25 | 0.13 | N/A | 0.20 | 0.12 | N/A |

These data show the average amount of 1-butene in the headspace of 250 mL jars that contain sheets of SB fiber that are dry, humidified 1 hour, and humidified 24 hours. The fiber sheets have been exposed to the atmosphere (20° C. and 50% RH) for varying lengths of time after pressurized exposure to 1-butene. Moisture content of samples was 0.17% prior to 1-butene pressurization.

1-Butene Desorption Data with and without Humidification for Film Stored in a Controlled Atmosphere of 50% Humidity for Six Weeks as a Function of Atmospheric Exposure

TABLE 4

| Atmospheric Exposure Time (hr) | Control Film Dry (ppm 1-butene) | Control Film Humidified 1 hr (ppm 1-butene) | Control Film Humidified 24 hr (ppm 1-butene) | Film Example 2 Dry (ppm 1-butene) | Film Example 2 Humidified 1 hr (ppm 1-butene) | Film Example 2 Humidified 24 hr (ppm 1-butene) |
|---|---|---|---|---|---|---|
| 24 | 0.17 | 0.09 | 0.21 | 0.34 | 5.01 | 5.57 |
| 96 | 0.35 | 0.27 | 0.29 | 0.33 | 4.55 | 6.22 |
| 144 | 0.64 | 0.35 | 0.38 | 1.03 | 3.54 | 4.83 |
| 288 | 0.00 | 0.00 | 0.07 | 0.00 | 2.99 | 3.73 |

These data show the average amount of 1-butene in the headspace of 250 mL jars that contain sheets of film that are dry, humidified 1 hour, and humidified 24 hours. The film sheets have been exposed to the atmosphere (20° C. and 50% RH) for varying lengths of time after pressurized exposure to 1-butene. Moisture content of samples was 0.13% prior to 1-butene pressurization. In the humidified samples of the invention the release of the 1-butene model compound was achieved through 288 hours or 12 days. In sharp contrast to the control samples containing no inhibitor and the dry samples, both failed to maintain an effective release in comparison to the examples of the invention 1-Butene Desorption Comparison of SB Fiber with 1-Butene complexed at 120 psig and 0 psig as a function of Atmospheric Exposure Time.

TABLE 5

| Atmospheric Exposure Time (hr) | SB Fiber Example 1 120 psig, 6 hr (ppm 1-butene) | SB Fiber Example 1 120 psig, 24 hr (ppm 1-butene) | SB Fiber Example 1 0 psig, 24 hr (ppm 1-butene) | SB Fiber Example 1 0 psig, 48 hr (ppm 1-butene) |
|---|---|---|---|---|
| 1 | — | 3.02 | 0.39 | 0.51 |
| 24 | — | 5.93 | 0.78 | 0.74 |

These data show the average amount of 1-butene in the headspace of 250 mL jars that contain fiber exposed to 1-butene at 120 psig for 6 hours and 24 hours, fiber exposed to 1-butene at 0 psig for 24 hours and 48 hours. In each case 75 sheets of 8.3×8.3 inch fiber webs per 3 Liter Tedlar bag with 150 ml of 1-butene gas at STP. Moisture content of fiber was <0.17% prior to complexation. The materials made at higher pressure released a greater amount of inhibitor.

1-Butene Desorption Comparison of Film with 1-Butene Complexed at 120 psig and 0 psig as a Function of Atmospheric Exposure Time.

TABLE 6

| Atmospheric Exposure Time (hr) | Film Ex. 2 120 psig, 6 hr (ppm 1-butene) | Film Ex. 2 120 psig, 24 hr (ppm 1-butene) | Film Ex. 2 0 psig, 24 hr (ppm 1-butene) | Film Ex. 2 0 psig, 48 hr (ppm 1-butene) |
|---|---|---|---|---|
| 1 | — | 5.28 | 1.02 | 1.64 |
| 24 | — | 6.35 | 1.25 | 2.05 |

These data show the average amount of 1-butene in the headspace of 250 mL jars that contain film exposed to 1-butene at 120 psig for 6 hours and 24 hours, film exposed to 1-butene at 0 psig for 24 hours and 48 hours. In each case 75 sheets of 4.0×4.0 inch films per 3 liter Tedlar bag with 150 ml of 1-butene gas at STP. Moisture content of film was <0.13% prior to complexation. The materials made at higher pressure released a greater amount of inhibitor.

1-Butene Desorption Data with and without Humidification for Coated Meltblown (MB) Fiber Samples as a Function of Atmospheric Exposure

TABLE 7

| Atmospheric Exposure Time (hr) | Ctrl Coated MB Dry (ppm 1-butene) | Ctrl Coated MB Humidified 1 hr (ppm 1-butene) | Ctrl Coated MB Humidified 24 hr (ppm 1-butene) | CD Coated MB Dry (ppm 1-butene) | CD Coated MB Humidified 1 hr (ppm 1-butene) | CD Coated MB Humidified 24 hr (ppm 1-butene) |
|---|---|---|---|---|---|---|
| 24 | 0.39 | 0.58 | 1.02 | 0.58 | 4.08 | 11.8 |
| 48 | 0.09 | 0.17 | 0.72 | 0.23 | 2.06 | 8.45 |

These data show the average amount of 1-butene in the headspace of 250 mL jars containing sheets of coated meltblown fiber that are dry, humidified 1 hour, and humidified 24 hours. The fiber sheets have been exposed to the atmosphere for 24 and 48 hours after pressurized exposure to 1-butene. Moisture content of samples was <0.18% prior to 1-butene pressurization for 24 hours. In the humidified samples of the invention coated MB samples the release of the 1-butene was greater than achieved with either spunbond fiber or film for the same period of atmospheric exposure time of 24 and 48 hours of atmospheric exposure of 20° C. and 50% relative humidity (RH). In sharp contrast to the control samples containing no inhibitor and the dry samples, both failed to maintain an effective release in comparison to the coated meltblown examples of the invention.

In summary, these data show that a humidified enclosed space containing the composition of the invention can lead to the release of an effective quantity of the olefinic inhibitor compound for an extended period of time up to twelve days of atmospheric exposure of 20° C. and 50% RH. The data further shows that the data support the effective release of complexed olefinic compound from film, fiber and coated fiber at high relative humidity achieved during storage of produce.

Film Description
Film Example 3
Tri-layer, Co-Ex Emil blown film
Outer layers: each layer 2 mil comprising:
2.0% α-cyclodextrin Cavamax W6A lot 60F203 grafted onto the polyolefin blend (Wacker Chemie)
21.5% Integrate NE542-013
38.2% Affinity PF1140G (Dow Plastics)
38.3% Affinity 8852G (Dow Plastics)
 Core: 2 mil Mobil LGA 105 LDPE
Procedure for Extracting 1-MCP Gas and Sample Preparation The 1-methylcyclopropene (1-MCP) was received in the form of a complex with cyclodextrin powder. The powder was estimated to contain 5 wt % 1-MCP. To extract the 1-MCP, 500 g of the powder was placed in a 3 L Tedlar bag along with a pouch containing 50 mL of D.I. water. The bag was sealed and the lab air was evacuated from it. Once sealed and evacuated, the pouch of water was popped, putting the water in contact with the powder. Gaseous 1-MCP is produced from the CD/1-MCP complex when exposed to high humidity. After a period of time, the bag filled with 1-MCP gas. 150 mL gaseous 1-MCP was then extracted from the bag via syringe and injected into another sealed and evacuated 3 L Tedlar bag that contained 75 sheets of film. This bag was then placed in a pressure vessel. The vessel was pressurized to 120±5 psig. The vessel was held at this pressure for 40 hours. After this period, the films were removed from the vessel and bag and set out in either a controlled laboratory atmosphere (20° C., 50% RH) or a desiccator.

Testing Procedure
1. Film exposed to lab atmosphere or stored in a desiccator—6, 24, 168 hours.
2. One film sample per 250 ml jar
3. Jar headspace sampled when dry, humidified 1 hr, and humidified 24 hr After being stored in either the lab atmosphere or desiccator for the desired amount of time, one film sample was placed in a 250 mL jar. The jar was allowed to sit for 1 hour at 20° C. Then, a 1 mL aliquot of the jar headspace was put onto a fused silica PLOT column. After this headspace sample was taken, 50 µL of deionized water was injected into the jar to create a 100% humid atmosphere in side the jar. Care was taken so that the water did come in direct contact with the sample. One hour after injection of the water a second headspace sample was analyzed. A final headspace sample was analyzed 24 hours after the injection of water. The gas chromatographs generated were used to determine the 1-MCP content in the jar.

Data for Film Pressurized with 1-MCP

TABLE 1

The average amount of 1-MCP in the headspace of 250 mL jars that contain film sheets of 1-MCP pressurized Example 2 film that is dry, humidified 1 hour, and humidified 24 hours. The moisture content of the film was <0.08% prior to 1-MCP pressurization.

| Exposure Time (hr) | Ex. 2 Lab Exposed Dry (ppm 1-MCP) | Ex. 2 Lab Exposed Humidified 1 hr (ppm 1-MCP) | Ex. 2 Lab Exposed Humidified 24 hr (ppm 1-MCP) | Ex. 2 Desiccator Exposed Dry (ppm 1-MCP) | Ex. 2 Desiccator Exposed Humidified 1 hr (ppm 1-MCP) | Ex. 2 Desiccator Exposed Humidified 24 hr (ppm 1-MCP) |
|---|---|---|---|---|---|---|
| 6 | 0.00 | 0.97 | 1.02 | 0.00 | 1.20 | 1.23 |
| 24 | 0.00 | 0.93 | 0.94 | 0.00 | 1.13 | 1.11 |
| 168 | 0.00 | 0.97 | 1.00 | 0.00 | 1.35 | 1.23 |

The data further show the importance of using dry thermoplastic and coating materials to introduce the inhibitor compound into the interior of the central pore of a cyclodextrin compound at increased pressure.

The foregoing discloses embodiments of the invention. In the Specification and claims, "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. "Optional" or "optionally" means that the subsequently described event or circumstance may but need not occur, and that the description includes instances where the event or circumstance occurs and instances in which it does not. The present invention may suitably comprise, consist of, or consist essentially of, any of the disclosed or recited elements. Thus, the invention illustratively disclosed herein can be suitably practiced in the absence of any element which is not specifically disclosed herein. The use of the singular typically includes and at least does not exclude the plural.

The specification, figures, examples and data provide a detailed explanation of the invention as it has been developed to date. The invention, however, can take the form of nonwovens, fibers, films, sheets, bottles, caps, and other embodiments without departing from the spirit or the intended scope of the invention. The invention therefore resides in the appended claims.

We claim:

1. A controlled release composition comprising: a cyclodextrin modified thermoplastic polymer comprising a cyclodextrin moiety covalently bonded to a thermoplastic polymer; and 1-methylcyclopropene complexed with the cyclodextrin moiety, wherein the controlled release composition is formed by contacting the cyclodextrin modified thermoplastic polymer comprising less than 800 ppm of water with gaseous 1-methylcyclopropene wherein the contacting is at a molar ratio of about 0.5 moles to about 10 moles of 1-methylcyclopropene per mole of the cyclodextrin moiety, in an enclosed space, at a pressure of about 1 atmosphere to about 15 atmospheres, and at a temperature of about 0° C. to 100° C.

2. The controlled release composition of claim 1 wherein the enclosed space comprises less than about 5 ppm water.

3. The controlled release composition of claim 1 wherein the pressure is about 120 psig.

4. The controlled release composition of claim 1 wherein the contacting is carried out for about 40 hours.

5. The controlled release composition of claim 1 wherein the cyclodextrin modified thermoplastic polymer comprises a cyclodextrin moiety covalently bonded to a polyolefin.

6. The controlled release composition of claim 1 wherein the composition comprises about 0.1 wt % to 20 wt % cyclodextrin.

7. The composition of claim 1 further comprising a thermoplastic polymer, wherein the thermoplastic polymer is contacted with the cyclodextrin modified thermoplastic polymer prior to the contacting with 1-methylcyclopropene.

8. The composition of claim 7 wherein the composition comprises about 1 wt % to 65 wt % of the cyclodextrin modified thermoplastic polymer.

9. The composition of claim 7 wherein the composition comprises about 0.0001 wt % to 3 wt % 1-methylcyclopropene.

10. The composition of claim 7 wherein the cyclodextrin modified thermoplastic polymer comprises a cyclodextrin modified polyolefin and the thermoplastic polymer comprises a polyolefin resin.

* * * * *